United States Patent
Schwager

(10) Patent No.: US 9,549,981 B2
(45) Date of Patent: Jan. 24, 2017

(54) SEQUENTIAL ANTIBODY THERAPY

(75) Inventor: Kathrin Schwager, Zurich (CH)

(73) Assignee: Philogen S.p.A., Sovicille (IT)

( * ) Notice: Subject to any disclaimer, the term of this patent is extended or adjusted under 35 U.S.C. 154(b) by 256 days.

(21) Appl. No.: 14/233,456

(22) PCT Filed: Jun. 22, 2012

(86) PCT No.: PCT/EP2012/062073
§ 371 (c)(1),
(2), (4) Date: Mar. 13, 2014

(87) PCT Pub. No.: WO2013/010749
PCT Pub. Date: Jan. 24, 2013

(65) Prior Publication Data
US 2014/0193908 A1 Jul. 10, 2014

(30) Foreign Application Priority Data

Jul. 19, 2011 (EP) .................................. 11005902

(51) Int. Cl.
*A61K 39/395* (2006.01)
*A61K 38/20* (2006.01)
*C07K 16/18* (2006.01)
*C07K 16/28* (2006.01)
*A61K 47/48* (2006.01)
*C12N 5/09* (2010.01)

(52) U.S. Cl.
CPC ..... *A61K 39/39558* (2013.01); *A61K 38/2013* (2013.01); *A61K 39/39541* (2013.01); *A61K 47/48561* (2013.01); *C07K 16/18* (2013.01); *C07K 16/2818* (2013.01); *C12N 5/0693* (2013.01); *C07K 2319/33* (2013.01)

(58) Field of Classification Search
None
See application file for complete search history.

(56) References Cited

U.S. PATENT DOCUMENTS

| | | | | |
|---|---|---|---|---|
| 8,110,194 | B2 * | 2/2012 | Nichol | C07K 16/2818 424/155.1 |
| 2003/0166163 | A1 * | 9/2003 | Gillies | C07K 14/55 435/69.52 |
| 2006/0246123 | A1 * | 11/2006 | Gilboa | C07H 21/00 424/450 |
| 2009/0117132 | A1 * | 5/2009 | Readett | A61K 39/39541 424/172.1 |
| 2011/0081354 | A1 * | 4/2011 | Korman | A61K 39/3955 424/152.1 |
| 2011/0250170 | A1 * | 10/2011 | Pedretti | A61K 38/2013 424/85.2 |
| 2011/0318302 | A1 | 12/2011 | Schwager et al. | |
| 2014/0294758 | A1 * | 10/2014 | Gillies | A61K 47/48569 424/85.2 |

FOREIGN PATENT DOCUMENTS

WO 2010/078945 A2 7/2010

OTHER PUBLICATIONS

Malki et al., 2014, Tumor Angiogenesis and Anti-Angiogenic Therapy, p. 1-9. In: Cancer Treatment Strategies, OMICS Group eBooks.*
Chin et al., Chang Gung Med J 2008, 31:1-15.*
Johannsen et al. (Eur. J. Cancer 2010, 46: 2926-2935).*
Natharajan et al. (Drugs 2011 (Jul. 9), 71(10): 1233-1250).*
Carnemolla et al. (Blood 2002, 99: 1659-1665).*
Hanlin et al. (Cancer Research 2003, 63: 3202-3210).*
Pedersen et al. (Cancer Letters 2006, 235: 229-238).*
Hurwitz et al. Proc Natl Acad Sci U S A. 1998; 95(17): 10067-10071.*
International Search Report dated Sep. 11, 2012 issued in corresponding PCT/EP2012/062073 application (pp. 1-4).
P.A. Prieto et al., "Cytotoxic T Lymphocyte-Associated Antigen 4 Blockade with Ipilimumab: Long-Term Follow-Up of 179 Patients with Metastatic Melanoma", Journal of Clinical Oncology, vol. 28, No. 15 (2010) XP-002682167 p. 1.
A.V. Maker et al., "Tumor Regression and Autoimmunity in Patients Treated With Cytotoxic T Lymphocyte-Associated Antigen 4 Blockade and Interleukin 2: A Phase I/II Study", Annals of Surgical Oncology, vol. 12, No. 12 (Dec. 2005) pp. 1005-1016.
A. Tarhini et al., "Releasing the Brake on the Immune System: Ipilimumab in Melanoma and Other Tumors", Cancer Biotherapy and Radiopharmaceuticals, vol. 25, No. 6 (2010) pp. 601-613.
C. Schliemann et al., "Complete Eradication of Human B-Cell Lymphoma Xenografts Using Rituximab in Combination with the Immunocytokine L19-IL2", Blood, American Society of Hematology, vol. 113, No. 10 (Mar. 2009) pp. 2275-2283.

* cited by examiner

*Primary Examiner* — Ilia Ouspenski
(74) *Attorney, Agent, or Firm* — Millen White Zelano and Branigan, PC; Csaba Henter; Anthony Zelano

(57) ABSTRACT

The invention provides a blocking ligand specific for CTLA-4 and a vascular targeting ligand/IL-2 complex, for sequential use in inhibiting the growth of tumor cell.

17 Claims, 2 Drawing Sheets

SEQUENTIAL ANTIBODY THERAPY

The present invention relates to the treatment of malignancies using a combined therapeutic approach. The invention makes use of vascular targeting antibodies fused to IL-2 and anti-CTLA-4 antibodies. In accordance with the invention, the antibodies are administered sequentially to a subject.

INTRODUCTION

Cytotoxic T lymphocyte associated antigen-4 (CTLA-4), which is a well-established negative regulator of the T cell response and is also known as CD152, is critical for the maintenance of T cell homeostasis and self-tolerance. The mechanisms by which CTLA-4 exerts its immune inhibitory function are multifaceted and can occur directly via conventional effector T cells or indirectly via regulatory T cells.

CTLA-4 is homologous to the co-stimulatory molecule CD28 and shares the same ligands, CD80 (B7.1) and CD86 (B7.2), which are expressed on the surface of antigen presenting cells (APCs). However, differential binding of CD80/CD86 on APCs to CD28 and CTLA-4 on effector T cells leads to opposing outcomes, with CD28 triggering T cell activation and CTLA-4 causing T cell inhibition. One mechanism by which CTLA-4 may induce T cell inhibition involves recruitment of the phosphatases SHP-1 and PP2A to the vicinity of the TCR in the immune synapse. This recruitment may result in dephosphorylation of the signalling molecules within the TCR complex and consequent termination of T cell activation.

Cancer immunotherapy relies on the ability of the immune system to target tumor specific antigens to generate an immune response. This initial response requires both binding of the MHC/antigen peptide to T-cell receptor complex along with a second co-stimulatory signal created by the binding of CD28 on the T cell with B7 located on the antigen presenting cell (Sharpe, A. H. and Abbas, A. K. (2006) *N Engl J Med* 355, 973-975.). Regulatory checkpoints, such as cytotoxic T-lymphocyte-associated antigen-4 (CTLA-4), serve to attenuate this signal, thereby preventing autoimmunity. CTLA-4 provides a potent inhibitory signal to the immune response that dampens lymphocyte activation (Ribas, A. (2007) *Update Cancer Ther,* 2, 133-139; Walunas, et al., (1994) *Immunity,* 1, 405-413).

Its key role in regulating the immune system has made CTLA-4 an attractive therapeutic target for cancer, with the development of fully human monoclonal antibodies that block CTLA-4. Anti-CTLA-4 monoclonal antibodies such as ipilimumab result in the blockade of CTLA-4 signalling, thereby prolonging T-cell activation, restoring T-cell proliferation, and thus amplifying T-cell mediated immunity (Peggs et al., (2007) *Update Cancer Ther,* 2, 133-139). Promising preclinical data in mouse models led to the investigation of two fully human monoclonal anti-CTLA-4 antibodies in patients with advanced melanoma. Tremelimumab (an IgG2 antibody) and ipilimumab (an IgG1 antibody) have been investigated in phase II and III trials in patients with metastatic melanoma. Ipilimumab was approved by FDA in March 2011 as a second line treatment for advanced melanoma.

The compounds were administered either as monotherapy or in combination with peptide vaccines, dacarbazine chemotherapy or following whole-cell vaccination strategies. These trials achieved initial encouraging results of 6-21% clinical response rates. However, grade III and IV inflammatory toxicities were observed.

Interleukin-2 (IL-2), a four a helix bundle proinflammatory cytokine (WO01/082298) produced by T helper 1 cells, plays an essential role in the activation phases of both specific and natural immune responses (Taniguchi et al. Cell 73:5-8, 1993). IL-2 promotes proliferation and differentiation of activated T and B lymphocytes and of natural killer (NK) cells, and induces cytotoxic T cell (CTL) activity and NK/lymphokine activated killer (LAK) antitumor cytotoxicity. IL-2 has been used in immunotherapy approaches of several human tumours (Rosenberg J. Clin. Oncol. 10:180-199, 1992). Administration of recombinant IL-2 (rIL2) alone or in combination with adoptively transferred lymphoid cells has resulted in the regression of established tumours in both animal models and patients.

However, its in vivo therapeutic efficacy is limited by its rapid clearance and, at high doses, by a severe toxicity mainly related to a vascular leak syndrome (Siegel and Puri, (1991) J. Clin. Oncol, 9:694-704). Delivery of IL-2 to the tumor site by means of an antibody directed against a cell-surface tumor marker may allow achievement of active local concentrations of IL-2, as well as reducing toxicities associated to systemic administration (Lode et al. Pharmacol Ther. 80:277-292, 1998).

The anti-CTLA-4 antibody ipilimumab has been combined with high dose IL-2 in a Phase I/II study. There were 8 objective responders (3 complete and 5 partial) out of 36 patients (22%). The authors concluded that this data did not seem to support a synergistic effect of IL-2 and anti-CTLA-4 antibodies, since treatment with either agent alone could obtain the observed response rate, or it could be an additive effect (Maker, et al., (2005) *Ann Surg Oncol,* 12, 1005-1016.). Ipilimumab is marketed by BMS as Yervoy, and is approved for melanoma.

Another anti-CTLA-4 antibody is available, tremelimumab (Pfizer). This antibody is in development for melanoma and other cancers.

The L19 antibody, specific to the alternatively-spliced extradomain B of fibronectin (EDB), a marker of angiogenesis (WO99/058570) (Neri, D. and Bicknell, R. (2005) *Nat Rev Cancer,* 5, 436-446; Schliemann, G. and Neri, D. (2007) *Biochim Biophys Acta,* 1778, 175-192) is one of the most validated vascular targeting agents, having been studied alone and as antibody derivative in many biodistribution and therapy studies, in animal models of cancer and in patients (Santimaria, et al. (2003) *Clin Cancer Res,* 9, 571-579; Sauer, et al. (2009) *Blood,* 113, 2285-2274).

L19-IL2 is a recombinant fusion protein composed of the human antibody fragment scFv(L19) fused to human IL-2. Recombinant IL-2, or Proleukin™ (Novartis) has been approved in the EU for the treatment of renal cell carcinoma (RCC) and in the United States for the treatment of RCC and melanoma. The potency of L19-IL2 is equivalent to the potency of IL-2.

The therapeutic performance of L19-IL2 has been extensively tested in various mouse models of cancer, including transplanted pancreatic and liver tumours ("orthotopic" models) (Carnemolla, et al., (2002) *Blood,* 99, 1659-1665, Menrad, A. and Menssen, H. D. (2005) *Expert Opin Ther Targets,* 9, 491-500, Schliemann, et al., (2009) *Blood,* 113, 2275-2283, Wagner, et al., (2008) *Clin Cancer Res,* 14, 4951-4980). In rodent models, L19-IL2 exhibited a preferential uptake around newly formed blood-vessels, with tumor-to-blood ratios of up to 30-to-1 as soon as 24 hours after injection whereas IL-2 fused to antibodies of irrelevant specificity did not exhibit preferential uptake in the tumor mass (Carnemolla, et al., (2002) *Blood,* 99, 1659-1685).

L19-IL2 is currently investigated in Phase I and II clinical trials for different malignancies (Johannsen, et al. (2010) *Eur J Cancer,* 46, 2926-2935) with a main focus in metastatic melanoma.

Similar to L19-IL2, other IL-2-based immunocytokines have been developed. F16-IL2 is composed of the human antibody F16 in scFv format fused to IL-2 (WO06/050834). F16 binds to the domain A1 of Tenascin C (Brack, et al., (2006). *Clin Cancer Res,* 12, 3200-3208). The immunocytokine F8-IL2 is composed of the human antibody F8, specific to extradomain A of fibronectin, and IL-2 (Frey, et al., (2010) *J Urol,* 184, 2540-2548; Villa, et al., (2008) *Int J Cancer,* 122, 2405-2413).

The rationale for the development of these products derives from the observation that F16-IL2 and F8-IL2 have exhibited selective localization at tumor sites in certain animal models of cancer. In particular, the F16 antibody appears to react more with tissue sections of head and neck cancer, breast cancer and lung cancer compared to the L19 antibody (Frey, et al., 2010, Marlind, et al., (2008) *Clin Cancer Res,* 14, 8515-6524, Pedretti, et al., (2009) *Lung Cancer.* 64, 28-33).

It has been previously been shown in F9 teratocarcinoma bearing mice that combination of IL12-IL19 with an anti-CTLA-4 antibody was clearly more effective than single agent treatment (Halin, et al., (2003) *Cancer Res,* 63, 3202-3210). However, the combination of L19-IL2 and anti-CTLA-4 has never been tested before.

SUMMARY OF THE INVENTION

We have shown that combination therapy with a vascular targeting antibody fused to IL-2 and an anti-CTLA-4 antibody has a synergistic effect in the treatment of tumours. In an embodiment of the invention, a synergistic effect is associated with sequential use of the two antibodies, in which the anti-CTLA-4 antibody is administered before the IL-2 conjugate.

In a first aspect, therefore, there is provided a blocking ligand specific for CTLA-4 and a vascular targeting ligand/IL-2 complex, for sequential use in inhibiting the growth of tumour cells.

CTLA-4 is understood responsible for attenuating the T-cell mediated immune response; in the immune synapse, CD28 upregulates, whilst CTLA-4 downregulates, T-cell expansion. Accordingly, the ligand specific for CTLA-4 is capable of blocking CTLA-4, or otherwise preventing activation of CTLA-4 and thus preventing downregulation of T-cell expansion. CTLA-4 blocking ligands are known, and include antibodies specific for CTLA-4 and RNA aptamers specific for CTLA-4. Other ligands, such as CD80 and CD86, bind to CTLA-4 and are responsible for activating CTLA-4 and potentiating its activity in downregulation of T-cell proliferation.

In one embodiment, the blocking ligand specific for CTLA-4 is selected from an antibody, a peptide and a nucleic acid aptamer specific for CTLA-4.

Antibodies which block CTLA-4 include ipilimumab and tremelimumab, as well as 9H10 (eBioScience, San Diego, Calif.) and other anti-CTLA-4 antibodies which are available in the art.

In one embodiment, the vascular targeting ligand is selected from an antibody and a peptide specific for a vascular marker. Vascular targeting has been described in the art for the treatment of cancer. Approaches suitable for use in the present invention include the use of antibodies, peptides, RNA aptamers and growth factors such as VEGF-A.

In one embodiment, the vascular targeting ligand is an antibody. The antibody may be an antibody fragment, as described below, such as a scFv.

The vascular targeting ligand may be targeted to any marker which is expressed in tumour vasculature. Examples include MHC class II, VCAM-I, fibronectin, the prostate-specific membrane antigen, the VEGF receptor, CD44-related antigen (TES-23), and the like.

IL-2 can be complexed with a vascular targeting ligand according to known techniques, for example as described in WO01/62298.

In one embodiment, the vascular targeting ligand is specific for the alternatively spliced extradomain B of fibronectin, domain A1 of tenascin C, or extradomain A of fibronectin. In one embodiment, the vascular targeting ligand/IL-2 complex is L19-IL2 (Carnemolla, et al., (2002) *Blood,* 99, 1659-1685, Menrad, A. and Menssen, H. D. (2005) *Expert Opin Ther Targets,* 9, 491-500, Schliemann, et al., (2009) *Blood,* 113, 2275-2283, Wagner, et al., (2008) *Clin Cancer Res,* 14, 4951-4960).

The order of administration of the ligands has an effect on the therapeutic potential of the ligands described in the present invention. Although tumour growth retardation is observed when the ligands are administered, in either order, a reduction in tumour mass is only observed when the ligand specific for CTLA-4 is administered before the vascular targeting ligand/IL-2 complex.

In one embodiment, therefore, the tumour cells are part of a solid tumour, and treatment results in reduction in tumour size.

The timing of the administration may be chosen according to empirically-determined criteria; in one embodiment, however, the ligand specific for CTLA-4 is administered one day before the vascular targeting ligand/IL-2 complex.

In a further embodiment, the administration of both the ligand specific for CTLA-4 and the vascular targeting ligand/IL-2 complex is repeated.

For example, the repeat administrations occur four days apart.

In a second aspect, the invention relates to a method for inhibiting the growth of a tumour cell, comprising contacting said cell with a ligand specific for CTLA-4 and a vascular targeting ligand/IL-2 complex according to the first aspect of the invention.

DETAILED DESCRIPTION OF THE INVENTION

Figure 1:
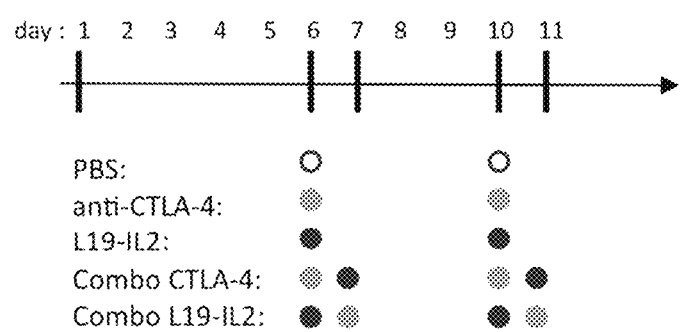
FIG. 1: Treatment schedule. 5 groups of mice received injections on day 6/7 and 10/11 after tumor implantation. In the first combination group anti-CTLA-4 treatment was administered 1 day before L19-IL2 (Combo anti-CTLA-4), whereas in the second combination group L19-IL2 was given first (Combo L19-IL2).
Figure 2:
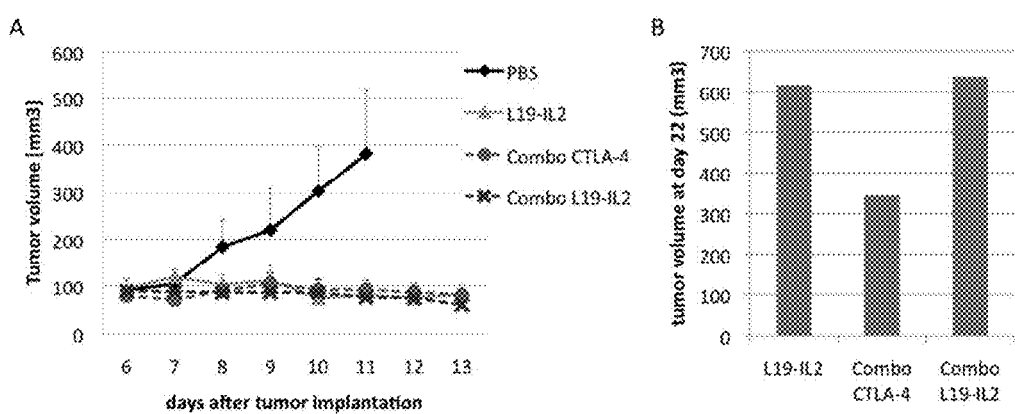
FIG. 2: Therapy results. A) No therapeutic effect could be observed with the anti-CTLA-4 antibody alone (not shown). L19-IL2 and the two combination groups showed long lasting tumor growth retardation. B) At day 22 after tumor implantation the average tumor size in the Combo CTLA-4 group was clearly reduced (50%) compared to the L19-IL2 monotherapy and the Combo L19-IL2 group.

Unless otherwise stated, all technical and scientific terms used herein have the same meanings as commonly understood by one of ordinary skill in the art to which this invention belongs. Any methods and materials with similar or equivalent function to those described herein can be used in the practice or testing of the present invention. Methods, devices, and materials suitable for such uses are now described. All publications cited herein are incorporated herein by reference in their entirety for the purpose of describing and disclosing the methodologies, reagents, and tools reported in the publications that might be used in connection with the invention.

The methods and techniques of the present application are generally performed according to conventional methods well known to those of skill in the art and as described in various general and more specific references that are cited and discussed throughout the present specification unless otherwise indicated. Such techniques are explained fully in the literature. See, e.g., Gennaro, A, R., ed. (1990) Remington's Pharmaceutical Sciences, 18th ed., Mack Publishing Co.; Hardman, J. G., Limbird, L. E., and Oilman, A. G., eds. (2001) The Pharmacological Basis of Therapeutics, 10th ed., McGraw-Hill Co.; Colowick, S. et al., eds., Methods In Enzymology, Academic Press, Inc.; Weir, D. M., and Blackwell, C. C., eds. (1988) Handbook of Experimental Immunology, Vols. I-IV, Blackwell Scientific Publications; Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press; Newton, C. R., and Graham, A., eds. (1997) PCR (Introduction to Biotechniques Series), 2nd ed., Springer-Verlag.

A "ligand" according to the invention is any molecule that binds to a target. In the specific context for the invention, ligands are provided which bind to CTLA-4 and to a vascular target, such as fibronectin. Ligands may be antibodies, peptides, nucleic acids, proteins (such as growth factors), and the like, which have the desired property of binding to a specific target, such as an antigen or a receptor. Ligands may comprise antibody and non-antibody ligands in any combination. For example, the CTLA-4 ligand may be an anti-CTLA-4 antibody, and the vascular targeting ligand may be the L19 antibody. The L19 antibody is described, for example, in WO01/62298 or Pini et al., (1998) J. Biol. Chem. 273:21769-21776.

A "blocking" ligand is one that attenuates, as opposed to potentiates, the activity of CTLA-4. For example, a ligand such as CD80 potentiates the activity of CTLA-4, but an anti-CTLA-4 antibody blocks CTLA-4.

A ligand, in one embodiment, binds to a target specifically. Specific binding is the ability to bind to the cognate target with a higher degree of affinity and/or avidity that to other targets. As such, ligands may be members of a specific binding pair, made up of the ligand and its cognate target. Ligands may also be referred to as specific binding members, for instance as in WO01/82298.

A "ligand/IL-2 complex" is a complex comprising a ligand and IL-2. IL-2 may be conjugated to the ligand by any known means, but in one embodiment is conjugated using a peptide bond and can be constructed as a fusion protein with the ligand. In one embodiment, IL-2 can be substituted with another proinflammatory cytokine, such as IL-1, IL-6, TNFα, IL-12, Interferons, IL-15 and KGF-1.

The term "antibody", unless indicated otherwise, is used to refer to entire antibodies as well as antigen-binding fragments of such antibodies. For example, the term encompasses four-chain IgG molecules, as well as antibody fragments.

As used herein, the term "antibody fragments" refers to portions of an intact full length antibody—such as an antigen binding or variable region of the intact antibody. Examples of antibody fragments include Fab, Fab', F(ab')2, and Fv fragments; diabodies; linear antibodies; single-chain antibody molecules (e.g., scFv); multispecific antibody fragments such as bispecific, trispecific, and multispecific antibodies (e.g., diabodies, triabodies, tetrabodies); binding-domain immunoglobulin fusion proteins; camelized antibodies; minibodies; chelating recombinant antibodies; tribodies or bibodies; intrabodies; nanobodies; small modular immunopharmaceuticals (SMIP), $V_{HH}$ containing antibodies; and any other polypeptides formed from antibody fragments, for example as further described below.

Antibodies may be of any class, such as IgG, IgA or IgM; and of any subclass, such as IgG1 or IgG4. Different classes and subclasses of immunoglobulin have different properties, which may be advantageous in different applications.

Specificity, in the context of the present invention, requires that the claimed antibody be capable of selectively binding its defined cognate antigen, which is either CTLA-4 or a vascular target.

An "aptamer" is a nucleic acid molecule or a polypeptide which is capable of binding to a specific target. Aptamers can be derived by selection, for instance by the SELEX procedure.

"Nucleic acids" as referred to herein typically include DNA molecules which encode the antibodies of the invention. Preferred are expression vectors, which are suitable for expressing the antibody genes in a host cell. Expression vectors and host cells for antibody gene expression are known in the art; see, for example, Morrow, K. J. (2008) Genetic Engineering & Biotechnology News. (Jun. 15, 2008) 28(12), and Backliwal, G., et al. (2008) Nucleic Acids Res. 36(15): e96-e96.

"CTLA-4", as used herein, refers to mammalian CTLA-4. The sequence of human CTLA-4 can be found in GenBank, Accession number AAH74893.1, GI:49904741, Mammalian CTLA-4 can be selected from rodent, such as mouse, or human CTLA-4. Anti-CTLA-4 antibodies are known in the art, and available commercially.

Vascular targets or markers are, in one embodiment, targets such as antigens or receptors that are selectively up-regulated in tumour versus normal endothelial cells. See, for example, Thorpe, P. E., (2004) Clin. Cancer Res. 10:415-427. In one embodiment, the vascular target or marker is fibronectin, for example the extradomain B of fibronectin.

Tumour cells targeted by ligands according to the invention may be any tumour cells, but in one embodiment are cells which are part of a solid tumour. The tumour may be any solid tumour, including without limitation any one or more of the following: melanoma, neuroblastoma, colorectal carcinoma, renal carcinoma, lung, carcinoma, lung metastasis, breast carcinoma, high-grade astrocytoma (grade III, grade IV), meningioma and angioma.

Sequential use is the administration of the ligands according to the invention separately, in sequence, rather than together. In some embodiments, the ligands are administered according to a defined administration schedule. A day, as understood in the context of timing of administration, is about 24 hours. For example if two agents are administered a day apart, they may be administered at the same time of day, 24 hours apart. However, variations in the exact timing may be permissible, and for example a day may be as little as 12 hours, or as much as 36 hours.

For example, the two different ligands according to the invention may be administered between 12 and 24 hours apart, such as 12, 13, 14, 15, 16, 17, 18, 19, 20, 21, 22, 23 or 24 hours apart.

In one embodiment, the two different ligands according to the invention may be administered between 24 and 48 hours apart, such as 24, 25, 26, 27, 28, 29, 30, 31, 32, 33, 34, 35, 36, 37, 38, 39, 40, 41, 42, 43, 44, 45, 46, 47 or 48 hours apart.

Repeated administration is the administration of a ligand according to the invention more than once. For instance, an anti-CTLA-4 antibody may be administered at intervals of, for example, 1 or more days, such as 2, 3, 4, 5 or 6 days. In one embodiment, the anti-CTLA-4 antibody is administered repeatedly at an interval of 4 days. The vascular targeting ligand/IL-2 complex may be administered at the same, or a different, interval, separated from the anti-CTLA-4 ligand according to the schedule of administration as determined for sequential use.

1. Antibodies

The invention encompasses antigen-binding fragments of the antibodies set forth in the claims. Fragments of antibodies according to the invention are capable of binding the CTLA-4 or to a vascular marker. They encompass Fab, Fab', F(ab')$_2$, and F(v) fragments, or the individual light or heavy chain variable regions or portion thereof. Fragments include, for example, Fab, Fab', F(ab')$_2$, Fv and scFv. These fragments lack the Fc portion of an intact antibody, clear more rapidly from the circulation, and can have less non-specific tissue binding than an intact antibody. These fragments can be produced from intact antibodies using well known methods, for example by proteolytic cleavage with enzymes such as papain (to produce Fab fragments) or pepsin (to produce F(ab')$_2$ fragments).

The antibodies and fragments also encompass single-chain antibody fragments (scFv) that bind to CTLA-4 or a vascular marker. An scFv comprises an antibody heavy chain variable region ($V_H$) operably linked to an antibody light chain variable region ($V_L$) wherein the heavy chain variable region and the light chain variable region, together or individually, form a binding site that binds αβTCR. An scFv may comprise a $V_H$ region at the amino-terminal end and a $V_L$ region at the carboxy-terminal end. Alternatively, scFv may comprise a $V_L$ region at the amino-terminal end and a $V_H$ region at the carboxy-terminal end.

Furthermore, although the two domains of the Fv fragment, $V_L$ and $V_H$, are coded for by separate genes, they can be joined, using recombinant methods, by a synthetic linker that enables them to be made as a single protein chain in which the VL and VH regions pair to form monovalent molecules (known as single chain Fv (scFv)). An scFv may optionally further comprise a polypeptide linker between the heavy chain variable region and the light chain variable region.

The antibodies and fragments also encompass domain antibody (dAb) fragments as described in Ward, E. S. et al. (1989) Nature 341:544-546 which consist of a $V_H$ domain. The antibodies and fragments also encompass heavy chain antibodies (HCAb). These antibodies are reported to form antigen-binding regions using only heavy chain variable region, in that these functional antibodies are dimers of heavy chains only (referred to as "heavy-chain antibodies" or "HCAbs"). Accordingly, antibodies and fragments may be heavy chain antibodies (HCAb) that specifically bind to CTLA-4 or a vascular marker. The antibodies and fragments also encompass antibodies that are SMIPs or binding domain immunoglobulin fusion proteins specific for CTLA-4 or a vascular marker. These constructs are single-chain polypeptides comprising antigen-binding domains fused to immunoglobulin domains necessary to carry out antibody effector functions (see, WO 2005/017148).

The antibodies and fragments also encompass diabodies. These are bivalent antibodies in which $V_H$ and $V_L$ domains are expressed on a single polypeptide chain, but using a linker that is too short to allow for pairing between the two domains on the same chain. This forces the domains to pair with complementary domains of another chain and thereby creates two antigen-binding sites (see, for example, WO 93/11181). Diabodies can be bispecific or monospecific.

The antibody or antibody fragment thereof according to the invention does not cross-react with any target other than CTLA-4 or a vascular marker.

The antibody or fragment thereof may be modified in order to increase its serum half-life, for example, by adding molecules—such as PEG or other wafer soluble polymers, including polysaccharide polymers to increase the half-life.

The antibodies and fragments thereof may be bispecific. For example, bispecific antibodies may resemble single antibodies (or antibody fragments) but have two different antigen binding sites (variable regions). Bispecific antibodies can be produced by various methods—such as chemical techniques, "polydoma" techniques or recombinant DNA techniques. Bispecific antibodies may have binding specificities for at least two different epitopes, at least one of which is CTLA-4 or a vascular marker. The other specificity may be selected from any useful specificities, including for example specificity for human serum albumin for the extension of half-life in vivo.

In one embodiment, a bispecific antibody may be constructed in which a first specificity is directed to a vascular marker, and a second specificity to IL-2, thus providing a complex comprising a ligand specific for a vascular marker, and IL-2.

The L-19 antibody is described above. In one embodiment, the antibody specific for a vascular marker is the L19 antibody.

The anti-CTLA-4 antibody may be any of the anti-CTLA-4 antibodies described herein. Anti-CTLA-4 antibodies have been reviewed in the literature, for example in Melero et al., (2007) Nature Reviews Cancer, 7:95-106. Human and other mammalian anti-CTLA-4 antibodies are also available from commercial suppliers, such as Novus Biologicals (Littleton, Colo., USA), Millipore (Billerica, Mass., USA), eBioscience (San Diego, Calif., USA) and the like.

2. Antibody Production

Antibodies useful in the present invention may be obtained from commercial sources. However, it is also possible to produce antibodies using method which are well known in the art. Antibody production techniques include production in transgenic organisms such as goats (see Pollock et al. (1999) J. Immunol. Methods 231:147-157), chickens (see Morrow, K. J. J. (2000) Genet. Eng. News 20:1-55), mice (see Pollock et al., supra) or plants (see Doran, P. M. (2000) Curr. Opinion Biotechnol. 11:199-204, Ma. J. K-C. (1998) Nat. Med. 4:801-606, Baez, J. et al. (2000) BioPharm. 13:50-54, Stoger, E. et al. (2000) Plant Mol. Biol. 42:583-590). Antibodies may also be produced by chemical synthesis or by expression of genes encoding the antibodies in host cells.

A polynucleotide encoding the antibody is isolated and inserted into a replicable construct or vector such as a plasmid for further propagation or expression in a host cell. Constructs or vectors (e.g., expression vectors) suitable for the expression of a humanized immunoglobulin according to the invention are available in the art. A variety of vectors are available, including vectors which are maintained in single copy or multiple copies in a host cell, or which become integrated into the host cell's chromosome(s). The constructs or vectors can be introduced into a suitable host cell, and cells which express a humanized immunoglobulin can be produced and maintained in culture. A single vector or multiple vectors can be used for the expression of a humanized immunoglobulin. Polynucleotides encoding the antibody are readily isolated and sequenced using conventional procedures (e.g., oligonucleotide probes). Vectors that may be used include plasmid, virus, phage, transposons, minichromsomes of which plasmids are a typical embodiment. Generally such vectors further include a signal sequence, origin of replication, one or more marker genes, an enhancer element, a promoter and transcription termination sequences operably linked to the light and/or heavy chain polynucleotide so as to facilitate expression. Polynucleotides encoding the light and heavy chains may be inserted into separate vectors and introduced (e.g., by transformation, transfection, electroporation or transduction) into the same host cell concurrently or sequentially or, if desired both the heavy chain and light chain can be inserted into the same vector prior to such introduction. A promoter can be provided for expression in a suitable host cell. Promoters can be constitutive or inducible. For example, a promoter can be operably linked to a nucleic acid encoding a humanized immunoglobulin or immunoglobulin chain, such that it directs expression of the encoded polypeptide. A variety of suitable promoters for prokaryotic and eukaryotic hosts are available. Prokaryotic promoters include lac, tac, T3, T7 promoters for *E. coli;* 3-phosphoglycerate kinase or other glycolytic enzymes e.g., enolase, glyceraldehyde 3-phosphate dehydrogenase, hexokinase, pyruvate decarboxylase, phosphofructokinase, glucose 6 phosphate isomerase, 3-phosphoglycerate mutase and glucokinase. Eukaryotic promoters include inducible yeast promoters such as alcohol dehydrogenase 2, isocytochrome C, acid phosphatase, metallothionein and enzymes responsible for nitrogen metabolism or maltose/galactose utilization; RNA polymerase II promoters including viral promoters such as polyoma, fowlpox and adenoviruses (e.g., adenovirus 2), bovine papilloma virus, avian sarcoma virus, cytomegalovirus (in particular the immediate early gene promoter), retrovirus, hepatitis B virus, actin, rous sarcoma virus (RSV) promoter and the early or late Simian virus 40 and non-viral promoters such as EF-1 alpha (Mizushima and Nagata (1990) *Nucleic Acids Res.* 18(17):5322). Those of skill in the art will be able to select the appropriate promoter for expressing a humanized antibody or portion thereof of the invention.

Where appropriate, e.g., for expression in cells of higher eukaroytes, additional enhancer elements can be included instead of or as well as those found located in the promoters described above. Suitable mammalian enhancer sequences include enhancer elements from globin, elastase, albumin, fetoprotein, metallothionine and insulin. Alternatively, one may use an enhancer element from a eukaroytic cell virus such as SV40 enhancer, cytomegalovirus early promoter enhancer, polyoma enhancer, baculoviral enhancer or murine IgG2a locus (see WO 04/009823). Whilst such enhancers are typically located on the vector at a site upstream to the promoter, they can also be located elsewhere e.g. within the untranslated region or downstream of the polyadenylation signal. The choice and positioning of enhancer may be based upon compatibility with the host cell used for expression.

In addition, the vectors (e.g., expression vectors) typically comprise a selectable marker for selection of host cells carrying the vector, and, in the case of a replicable vector, an origin of replication. Genes encoding products which confer antibiotic or drug resistance are common selectable markers and may be used in prokaryotic (e.g., f3-lactamase gene (ampicillin resistance), Tet gene (tetracycline resistance) and eukaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated.

In eukaryotic systems, polyadenylation and termination signals are operably linked to polynucleotide encoding the antibody of this invention. Such signals are typically placed 3' of the open reading frame. In mammalian systems, non-limiting examples of polyadenylation/termination signals include those derived from growth hormones, elongation factor-1 alpha and viral (e.g., SV40) genes or retroviral long terminal repeats. In yeast systems, non-limiting examples of polydenylation/termination signals include those derived from the phosphoglycerate kinase (PGK) and the alcohol dehydrogenase 1 (ADH) genes. In prokaryotic systems polyadenylation signals are typically not required and it is instead usual to employ shorter and more defined terminator sequences. The choice of polyadenylation/termination sequences may be based upon compatibility with the host cell used for expression. In addition to the above, other features that can be employed to enhance yields include chromatin remodeling elements, introns and host-cell specific codon modification. The codon usage of the antibody of this invention thereof can be modified to accommodate codon bias of the host cell such to augment transcript and/or product yield (e.g., Hoekema, A. et al. (1987) *Mol. Cell Biol.* 7(8):2914-24). The choice of codons may be based upon compatibility with the host cell used for expression.

The invention thus relates to isolated nucleic acid molecules that encode the humanized immunoglobulins, or heavy or light chains, thereof, of this invention. The invention also relates to isolated nucleic acid molecules that encode an antigen-binding portion of the immunoglobulins and their chains.

The antibodies according to this invention can be produced, for example, by the expression of one or more recombinant nucleic acids encoding the antibody in a suitable host cell. The host cell can be produced using any suitable method. For example, the expression constructs (e.g., one or more vectors, e.g., a mammalian cell expression vector) described herein can be introduced into a suitable host cell, and the resulting cell can be maintained (e.g., in culture, in an animal, in a plant) under conditions suitable for expression of the construct(s) or vector(s). Host cells can be prokaryotic, including bacterial cells such as *E. coli* (e.g., strain DH5a™) (Invitrogen, Carlsbad, Calif.), PerC6 (Crucell, Leiden, NL) *B. subtilis* and/or other suitable bacteria; eukaryotic cells, such as fungal or yeast cells (e.g., *Pichia pastoris. Aspergillus* sp., *Saccharomyces cerevisiae, Schizosaccharomyces pombe, Neurospora crassa*), or other lower eukaryotic cells, and cells of higher eukaryotes such as those from insects (e.g., *Drosophila* Schnieder S2 cells, Sf9 insect cells) (WO 94/128087 (O'Connor)), BTI-TN-5B1-4 (High Five™) insect cells (Invitrogen), mammals (e.g., COS cells, such as COS-1 (ATCC Accession No. CRL-1650) and COS-7 (ATCC Accession No. CRL-1651), CHO (e.g., ATCC Accession No. CRL-9096), CHO DG44 (Urlaub, G. and Chasin, L. A. (1980) *Proc. Natl. Acad. Sci. USA,* 77(7):4216-4220), 293 (ATCC Accession No. CRL-1573), HeLa (ATCC Accession No. CCL-2), CVI (ATCC Accession No. CCL-70), WOP (Dailey, L., et al. (1985) *J. Virol.,* 54:739-749), 3T3, 293T (Pear, W. S., et al. (1993) *Proc. Natl. Acad, Sci. U.S.A.,* 90:8392-8398), NSO cells, SP2/0 cells, HuT 78 cells, and the like, or plants (e.g., tobacco, lemna (duckweed), and algae). See for example, Ausubel, F. M. et al., eds. *Current Protocols in Molecular Biology*, Greene Publishing Associates and John Wiley & Sons Inc. (1993). In some embodiments, the host cell is not part of a multicellular organism (e.g., plant or animal), e.g., it is an isolated host cell or is part of a cell culture.

Host cells may be cultured in spinner flasks, shake flasks, roller bottles, wave reactors (e.g., System 1000 from wavebiotech.com) or hollow fibre systems but it is preferred for large scale production that stirred tank reactors or bag reactors (e.g., Wave Biotech, Somerset, N.J. USA) are used particularly for suspension cultures. Typically stirred tank reactors are adapted for aeration using e.g., spargers, baffles or low shear impellers. For bubble columns and airlift reactors, direct aeration with air or oxygen bubbles may be used. Where the host cells are cultured in a serum-free culture medium, the medium can be supplemented with a cell protective agent such as pluronic F-68 to help prevent cell damage as a result of the aeration process. Depending on the host cell characteristics, microcarriers may be used as growth substrates for anchorage dependent cell lines, or the cells may be adapted to suspension culture. The culturing of host cells, particularly vertebrate host cells, may utilize a variety of operational modes such as batch, fed-batch, repeated batch processing (see Drapeau et al. (1994) *Cytotechnology* 15:103-109), extended batch process or perfusion culture, Although recombinantly transformed mammalian host cells may be cultured in serum-containing media such media comprising fetal calf serum (FCS), it is preferred that such host cells are cultured in serum-free media such as disclosed in Keen et al. (1995) *Cytotechnology* 17:153-163, or commercially available media such as ProCHO-CDM or UltraCHO™ (Cambrex N.J., USA), supplemented where necessary with an energy source such as glucose and synthetic growth factors such as recombinant insulin. The serum-free culturing of host cells may require that those cells are adapted to grow in serum-free conditions. One adaptation approach is to culture such host cells in serum containing media and repeatedly exchange 80% of the culture medium for the serum-free media so that the host cells learn to adapt in serum-free conditions (see, e.g., Scharfenberg, K. et al. (1995) *Animal Cell Technology; Developments Towards the 21st Century* (Beuvery, E. C. et al., eds), pp. 619-623, Kluwer Academic publishers). Antibodies according to the invention may be secreted into the medium and recovered and purified therefrom using a variety of techniques to provide a degree of purification suitable for the intended use. For example, the use of therapeutic antibodies of the invention for the treatment of human patients typically mandates at least 95% purity as determined by reducing SDS-PAGE, more typically 98% or 99% purity, when compared to the culture media comprising the therapeutic antibodies. In the first instance, cell debris from the culture media is typically removed using centrifugation followed by a clarification step of the supernatant using e.g., microfiltration, ultrafiltration and/or depth filtration. Alternatively, the antibody can be harvested by microfiltration, ultrafiltration or depth filtration without prior centrifugation. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC) (see U.S. Pat. No. 5,429,746) are available. In one embodiment, the antibodies of the invention, following various clarification steps, are captured using Protein A or G affinity chromatography followed by further chromatography steps such as ion exchange and/or HA chromatography, anion or cation exchange, size exclusion chromatography and ammonium sulphate precipitation. Typically, various virus removal steps are also employed (e.g., nanofiltration using e.g., a DV-20 filter). Following these various steps, a purified preparation comprising at least 10 mg/ml or greater, e.g., 100 mg/ml or greater of the antibody of the invention is provided and therefore forms an embodiment of the invention. Concentration to 100 mg/ml or greater can be generated by ultracentrifugation. Such preparations are substantially free of aggregated forms of antibodies of the invention.

Bacterial systems are particularly suited for the expression of antibody fragments. Such fragments are localized intracellularly or within the periplasm. Insoluble periplasmic proteins can be extracted and refolded to form active proteins according to methods known to those skilled in the art, see Sanchez et al. (1999) *J. Biotechnol.* 72:13-20; Cupit, P. M. et al. (1999) *Lett. Appl. Microbiol.* 29:273-277.

The present invention also relates to cells comprising a nucleic acid, e.g., a vector, of the invention (e.g., an expression vector). For example, a nucleic acid (i.e., one or more nucleic acids) encoding the heavy and light chains of a humanized immunoglobulin according to the invention, or a construct (i.e., one or more constructs, e.g., one or more vectors) comprising such nucleic acid(s), can be introduced into a suitable host cell by a method appropriate to the host cell selected (e.g., transformation, transfection, electroporation, infection), with the nucleic acid(s) being, or becoming, operably linked to one or more expression control elements (e.g., in a vector, in a construct created by processes in the cell, integrated into the host cell genome). Host cells can be maintained under conditions suitable for expression (e.g., in the presence of inducer, suitable media supplemented with appropriate salts, growth factors, antibiotic, nutritional supplements, etc.), whereby the encoded polypeptide(s) are produced. If desired, the encoded humanised antibody can be isolated, for example, from the host cells, culture medium, or milk. This process encompasses expression in a host cell (e.g., a mammary gland cell) of a transgenic animal or plant (e.g., tobacco) (see e.g., WO 92/03918).

3. Vascular Targeting

The use of ligands to target biological agents to the sites of tumours by targeting vascular markers is known in the art. For example see Thorpe et al., (2003) Cancer Res. 83:1144-1147; Thorpe, E. R., Clin. (2004) Cancer Res. 10:415-427; Neri and Bicknell, (2005) Nat Rev Cancer 5:438-446; Ahlskog et al., (2008) Q J Nucl. Med. Imaging 50:298-309; Gerber et al., (2009) MAbs 1:247-253.

A variety of targets and ligands have been described in connection with anti-tumour therapy, including MHC Class II (Huang et al., (1997) Science 275:547-550); VCAM-1 (Ran et al., (1998) Cancer Res, 58:4646-4653); the EB-D domain of fibronectin (Nilsson et al., (2001) Cancer Res. 81:711-716); prostate-specific membrane antigen (Liu et al., (2002) Cancer Res. 62:5470-5475); CD44-related antigen (TES-23; Tsunoda et al., (1999) Br. J, Cancer, 81:1155-1161); integrins (Ruegg et al., (2004) BBA 1654:51-67); and Annexin A1 (Oh et al., (2004) Nature 429:629-635). The use of VEGF to target the VEGF receptor and deliver a toxin has been described, for instance in Arora et al., (1999) Cancer Res., 59:183-188, and Ramakrishnan et al., (1996) Cancer Res., 58:1324-1330. The use of the L-19 antibody to target IL-12 to tumours has been described by Halin et al., (2002) Nat. Biotechnol., 20:264-289, and Carnemolla et al., (2002) Blood 99:1659-1865.

Antibodies, growth factors and other peptides have been described for targeting tumours. Other, non-peptide ligands include nucleic acid aptamers, as described in Santulli-Marotto et al., (2003) Cancer Res. 63:7483-7489. Aptamers may be derived by in vitro selection procedures, such as Selex.

Conjugation of IL-2 with a ligand suitable for vascular targeting can be carried out as noted above, by conjugating the ligand with the IL-2 molecule by means of a peptide bond, i.e. within a fusion polypeptide comprising the IL-2 molecule and the ligand, or a polypeptide chain component thereof. See Taniguchi et al. (1983) Nature 302, 305-310; Maeda et al. (1983) Biochem. Biophys, Res. Comm. 115: 1040-1047; Devos et al. (1983) Nucl. Acids Res. 11: 4307-4323 for IL-2 sequence information useful in preparation of a fusion polypeptide comprising IL-2.

Other means for conjugation include chemical conjugation, especially cross-linking using a bifunctional reagent (e.g. employing ADOUBLE-REAGENTS™; Cross-linking Reagents Selection Guide, Pierce).

4. Pharmaceutical Compositions

In a preferred embodiment, there is provided a pharmaceutical composition comprising an antibody according to the invention, or a ligand or ligands as defined herein according to the invention. Ligands may be immunoglobulins, peptides, nucleic acids or small molecules, as discussed herein. They are referred to, in the following discussion, as "compounds".

A pharmaceutical composition according to the invention is a composition of matter comprising a compound or compounds capable of modulating T-cell activity as an active ingredient. Typically, the compound is in the form of any pharmaceutically acceptable salt, or e.g., where appropriate, an analogue, free base form, tautomer, enantiomer racemate, or combination thereof. The active ingredients of a pharmaceutical composition comprising the active ingredient according to the invention are contemplated to exhibit excellent therapeutic activity, for example, in the treatment of graft-versus-host disease, when administered in amount which depends on the particular case.

In another embodiment, one or more compounds of the invention may be used in combination with any art recognized compound known to be suitable for treating the particular indication in treating any of the aforementioned conditions, for instance cancer. For example, ligands according to the invention may be coadminstered with chemotherapeutic agents. Accordingly, one or more compounds of the invention may be combined with one or more art recognized compounds known to be suitable for treating the foregoing indications such that a convenient, single composition can be administered to the subject. Dosage regima may be adjusted to provide the optimum therapeutic response.

For example, several divided doses may be administered daily or the dose may be proportionally reduced as indicated by the exigencies of the therapeutic situation. The active ingredient may be administered in a convenient manner such as by the oral, intravenous (where water soluble), intramuscular, subcutaneous, intranasal, intradermal or suppository routes or implanting (e.g., using slow release molecules).

Depending on the route of administration, the active ingredient may be required to be coated in a material to protect said ingredients from the action of enzymes, acids and other natural conditions which may inactivate said ingredient.

In order to administer the active ingredient by other than parenteral administration, it will be coated by, or administered with, a material to prevent its inactivation. For example, the active ingredient may be administered in an adjuvant, co administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and nhexadecyl polyethylene ether. Enzyme inhibitors include pancreatic trypsin.

Liposomes include water-in-oil-in-water CGF emulsions as well as conventional liposomes. The active ingredient may also be administered parenterally or intraperitoneally.

Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants.

The prevention of the action of microorganisms can be brought about by various antibacterial and antifungal agents, for example, parabens, chlorobutanol, phenol, sorbic acid, thirmerosal, and the like. In certain cases, it may be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active ingredient in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Various other materials may be present as coatings or to otherwise modify the physical form of the dosage unit. Of course, any material used in preparing any dosage unit form should be pharmaceutically pure and substantially non-toxic in the amounts employed. In addition, the active ingredient may be incorporated into sustained-release preparations and formulations.

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such as active material for the treatment of disease in living subjects having a diseased condition in which bodily health is impaired.

The principal active ingredients are compounded for convenient and effective administration in effective amounts with a suitable pharmaceutically acceptable carrier in dosage unit form. In the case of compositions containing supplementary active ingredients, the dosages are determined by reference to the usual dose and manner of administration of the said ingredients.

In order to facilitate delivery of peptide compounds, including antibodies, to cells, peptides may be modified in order to improve their ability to cross a cell membrane. For example, U.S. Pat. No. 5,149,782 discloses the use of fusogenic peptides, ion-channel forming peptides, membrane peptides, long-chain fatty acids and other membrane blending agents to increase protein transport across the cell membrane. These and other methods are also described in WO 97/37018 and U.S. Pat. No. 5,108,921, incorporated herein by reference. In a further aspect there is provided the active ingredient of the invention as hereinbefore defined for use in the treatment of disease either alone or in combination with art recognized compounds known to be suitable for treating the particular indication. Consequently there is provided the use of an active ingredient of the invention for the manufacture of a medicament for the treatment of disease associated with an aberrant immune response.

Moreover, there is provided a method for treating a condition associated with an aberrant immune response, comprising administering to a subject a therapeutically effective amount of a ligand identifiable using an assay method as described above. The invention is further described, for the purposes of illustration only, in the following example.

Example

Methods:

Tumor bearing mice were obtained by subcutaneous injection of F9 teratocarcinoma cells ($2\times10^7$) in the flank of 10-week old female 129/SvEv mice by s.c. injection. When tumours reached a size of 50-100 mm$^3$, mice were randomly grouped (n=5) and treatment was started. Mice were injected into the lateral tail vein with either 30 ug L19-IL2, 50 ug anti-CTLA4 antibody or PBS for two injections (day 6 and 10).

Mice were monitored daily, tumor volumes were measured three to four times per week with a digital caliper and calculated using the formula: volume=length×width$^2$×0.5. Animals were sacrificed when tumor volumes reached 2000 mm$^3$. Experiments were performed under a project license granted by the Veterinaeramt des Kantons Zuerich, Switzerland (169/2008).

Results:

To investigate whether combined administration of L19-IL2 and an anti-CTLA-4 antibody would result in enhanced antitumor activity, we performed a therapy experiment in immunocompetent 129SV mice, bearing s.c. grafted F9 teratocarcinoma. Groups of mice (5 animals) received injections on day 6/7 and 10/11 (see FIG. 1).

The combination of L19-IL2 and anti-CTLA-4 was tested in two different schedules in order to evaluate possible sequence dependent effects. In the first combination group anti-CTLA-4 treatment was administered 1 day before L19-IL2 (Combo anti-CTLA-4), whereas in the second combination group L19-IL2 was given first (Combo L19-SL2).

No therapeutic benefit could be shown for the anti-CTLA-4 antibody in this tumor model. L19-IL2 and the two combinations groups showed long lasting tumor growth retardation. One week after the last injection tumours start to regrow. However, in the combination group in which anti-CTLA-4 was administered one day before L19-IL2 a reduction of 50% of tumor size was observed compared to the other groups.

The invention claimed is:

1. A method for inhibiting the growth of a vascularized solid tumor in a subject, comprising administering to said subject an effective amount of a ligand specific for CTLA-4 and a vascular targeting ligand/IL-2 complex, wherein the ligand specific for CTLA-4 is an anti-CTLA-4 ligand having an antagonist effect, and wherein the ligand specific for CTLA-4 is administered before the vascular targeting ligand/IL-2 complex.

2. A method according to claim 1, wherein the ligand specific for CTLA-4 is selected from an antibody, a peptide and a nucleic acid aptamer specific for CTLA-4.

3. A method according to claim 2, wherein the ligand specific for CTLA-4 is a nucleic acid aptamer specific for CTLA-4.

4. A method according to claim 3, wherein the nucleic acid aptamer specific for CTLA-4 is an RNA aptamer.

5. A method according to claim 2, wherein the ligand specific for CTLA-4 is an anti-CTLA-4 antibody.

6. A method according to claim 5, wherein the antibody is a scFv.

7. A method according to claim 1, wherein the vascular targeting ligand is selected from an antibody and a peptide specific for a vascular marker.

8. A method according to claim 7, wherein the vascular targeting ligand is an antibody.

9. A method according to claim 8, wherein the vascular targeting ligand is specific for the alternatively spliced extradomain B of fibronectin, domain A1 of tenascin C, or extradomain A of fibronectin.

10. A method according to claim 1, wherein the treatment results in reduction in tumour size.

11. A method according to claim 10, wherein the ligand specific for CTLA-4 is administered one day before the vascular targeting ligand/IL-2 complex.

12. A method according to claim 1, wherein the administration of both the ligand specific for CTLA-4 and the vascular targeting ligand/IL-2 complex is repeated.

13. A method according to claim 12, wherein the repeat administrations occur four days apart.

14. A method according to claim 1, wherein the vascular targeting ligand is specific for the alternatively spliced extradomain B of fibronectin.

15. A method according to claim 5, wherein the vascular targeting ligand is specific for the alternatively spliced extradomain B of fibronectin.

16. A method according to claim 15, wherein the tumor is selected from the group consisting of melanoma, neuroblastoma, colorectal carcinoma, renal carcinoma, lung carcinoma, lung metastasis, breast carcinoma, grade III astrocytoma, grade IV astrocytoma, meningioma and angioma.

17. A method according to claim 1, wherein the tumor is selected from the group consisting of melanoma, neuroblastoma, colorectal carcinoma, renal carcinoma, lung carcinoma, lung metastasis, breast carcinoma, grade III astrocytoma, grade IV astrocytoma, meningioma and angioma.

* * * * *